United States Patent [19]

Kwiatkowski et al.

[11] Patent Number: 4,792,224
[45] Date of Patent: Dec. 20, 1988

[54] PHOTOCHROMIC COMPOUND AND ARTICLES CONTAINING THE SAME

[75] Inventors: Patricia L. Kwiatkowski, Akron; David A. Hunt, Copley, both of Ohio

[73] Assignee: PPG Industries, Inc., Pittsburgh, Pa.

[21] Appl. No.: 50,266

[22] Filed: May 14, 1987

Related U.S. Application Data

[63] Continuation-in-part of Ser. No. 935,904, Nov. 28, 1986, abandoned.

[51] Int. Cl.$^4$ .................... G02B 5/23; C07D 265/00
[52] U.S. Cl. .................................. 351/163; 252/586; 544/71; 350/409; 350/354
[58] Field of Search ............... 430/345; 252/586; 544/71; 350/409, 354; 351/163; 427/160

[56] References Cited

U.S. PATENT DOCUMENTS

| | | | |
|---|---|---|---|
| 3,562,172 | 2/1971 | Ono et al. | 252/300 |
| 3,578,602 | 5/1971 | Ono et al. | 252/300 |
| 3,703,398 | 11/1972 | Ono et al. | 544/70 X |
| 4,215,010 | 7/1980 | Hovey et al. | 252/584 |
| 4,287,337 | 9/1981 | Guglielmetti et al. | 544/6 |
| 4,342,668 | 8/1982 | Hovey et al. | 252/586 |
| 4,634,767 | 1/1987 | Hoelscher et al. | 544/71 |

FOREIGN PATENT DOCUMENTS

| | | | |
|---|---|---|---|
| 1927849 | 12/1970 | Fed. Rep. of Germany | 544/71 |
| 153690 | 1/1982 | German Democratic Rep. | 544/71 |
| 513975 | 12/1977 | U.S.S.R. | 544/70 |

OTHER PUBLICATIONS

Arnold & Paal, "Spektroskopische Strukturuntersuchungen An Heterozyklischen Spiroverbindungen", Tetrahedron vol. 27, pp. 1699-1713, 1971 (w/translation).

Organic Synthesis, vol. I., 2nd Ed., H. Gilman et al., John Wiley & Sons, pp. 411-413 (1941).

Journal of Organic Chemistry, vol. 28, pp. 2759-2752 (Oct. 1963).

Thesis; "Synthesis and Physico-Chemical Studies of New Oxygenated and Sulfurated Azaheterocyclic Spirochromenes with 5 or 6 Saturated Groups", by Michel Maguet, University of Bretagne Occidentale, submitted Jun. 27, 1980, Table of Contents, pp. 27-37, 65-68, 75-76, 79, 165-179 and 191-199. (w/translation).

*Primary Examiner*—Matthew A. Thexton
*Assistant Examiner*—Catherine S. Kilby
*Attorney, Agent, or Firm*—Irwin M. Stein

[57] ABSTRACT

Described are photochromic spiro (oxazolidine) substituted benzoxazine photochromic compounds and their use in plastic hosts to impart a photochromic response thereto. More particularly, there are described spiro (oxazolidine) pyrido benzoxazine and spiro (oxazolidine) naphthoxazine compounds and their use in substrates such as polymerizates of allyl digylcol carbonate.

19 Claims, No Drawings

PHOTOCHROMIC COMPOUND AND ARTICLES CONTAINING THE SAME

CROSS REFERENCE TO RELATED APPLICATIONS

This application is a continuation-in-part application of application Ser. No. 935,904, filed Nov. 28, 1986, now abandoned.

DESCRIPTION OF THE INVENTION

The present invention relates to novel photochromic compounds, and to compositions and articles containing such photochromic compounds. Photochromism is a reversible phenomenon illustrated by a compound which, when exposed to the radiation of light involving ultraviolet rays, such as sunlight or the light of a mercury lamp, changes color and then returns to its original color if the radiation is discontinued or the compound is stored in the dark Various types of photochromic compounds have been synthesized and suggested for use in applications in which a color change or darkening is induced by sunlight. In particular, spiro(indoline) naphthoxazine compounds, as described in U.S. Pat. Nos. 3,562,172, 3,578,602, 4,215,010, and 4,342,668, have been reported as useful in such applications. Such photochromic compounds either in crystalline form or in solution or dispersion in a transparent medium change rapidly from a colorless state to blue when exposed to sunlight or ultraviolet radiation and return to the original colorless state by being allowed to stand in the dark or in the absence of strong ultraviolet radiation.

DETAILED DESCRIPTION OF THE INVENTION

In accordance with the present invention, there are provided novel spiro(oxazolidine) substituted benzoxazine photochromic compounds represented by the following graphic formula I,

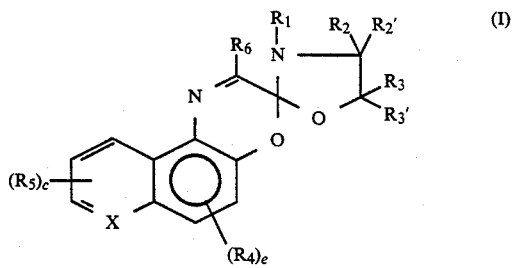

In the above graphic formula I, $R_1$ is selected from the group consisting of $C_1$-$C_8$ alkyl, e.g., methyl, ethyl, propyl, isopropyl, butyl, etc., $C_2$-$C_5$ alkenyl, e.g., allyl, phenyl, benzyl, and mono- and di-substituted phenyl, said phenyl substituents being selected from $C_1$-$C_4$ alkyl and $C_1$-$C_5$ alkoxy, e.g. methoxy, ethoxy, propoxy, butoxy and pentoxy. Preferably, $R_1$ is a $C_1$-$C_4$ alkyl, $C_2$-$C_3$ alkenyl, benzyl, or phenyl radical.

$R_2$, $R_2'$, $R_3$ and $R_3'$ of formula I are each selected from the group consisting of hydrogen, $C_1$-$C_5$ alkyl, $C_1$-$C_4$ alkoxyalkyl, phenyl, and mono- and di-substituted phenyl. The phenyl substituents may be selected from $C_1$-$C_4$ alkyl and $C_1$-$C_4$ alkoxy radicals. $R_2$ and $R_2'$, as well as $R_3$ and $R_3'$, may combine to form (including the spiro carbon atom) an alicyclic ring containing from 3 to 6 carbon atoms, i.e., a $C_3$-$C_6$ cycloalkyl, e.g., cyclopentyl. More particularly, $R_2$, $R_2'$, $R_3$ and $R_3'$ are each selected from hydrogen, $C_1$-$C_5$ alkyl, e.g., methyl, ethyl, propyl, butyl and pentyl, phenyl and methoxymethyl. When one of $R_2$ or $R_2'$ (or when one of $R_3$ or $R_3'$) is a tertiary alkyl radical, such as tertiary butyl or tertiary amyl, the ether is preferably an alkyl radical other than a tertiary alkyl radical.

$R_4$ and $R_5$ in graphic formula I are each selected from the group consisting of hydrogen, $C_1$-$C_5$ alkyl, $C_1$-$C_5$ alkoxy, phenyl, phenoxy, mono- and di-substituted phenoxy, nitro, cyano, $C_1$-$C_4$ monohaloalkyl, e.g., chloromethyl, $C_1$-$C_4$ polyhaloalkyl, e.g., $C_1$-$C_4$ trihaloalkyl such as trifluoromethyl, $C_1$-$C_4$ alkylsulfonyl, e.g., —$SO_2CH_3$ (methyl sulfonyl), trihaloacetyl, e.g., trichloroacetyl, benzoyl, benzoyloxy, and $C_1$-$C_4$ acyloxy, e.g., acetyloxy. The phenoxy substituents may be selected from an electron donating group such as alkyl, e.g., $C_1$-$C_4$ alkyl, alkoxy, e.g., $C_1$-$C_4$ alkoxy, amino, monoalkylamino and dialkylamino, e.g., alkylamino groups in which the alkyl radical contains from 1 to 6 carbon atoms, such as methylamino and dimethylamino; or electron withdrawing groups such as cyano, nitro, chloro, fluoro, and trihaloalkyl, e.g., $C_1$-$C_4$ trihaloalkyl such as trifluoromethyl. The letter "c" is a number from 0 to 4, e.g., 0 to 2, such as 1 or 2, the letter "e" is a number from 0 to 2, e.g., 0 or 1, and X is nitrogen or carbon.

When "e" is 2, or when "c" is 2 or more (and $R_4$ and $R_5$ are other than hydrogen) the $R_4$ and $R_5$ substituents may be the same or different and in either case are selected from the aforedescribed group of substituents. When $R_5$ is other than hydrogen and "c" is one, the $R_5$ substituent may be located on any of the available carbon atoms of that portion of the compound. Thus, when X is carbon, the $R_5$ substituent may be located at the 7', 8', 9' or 10' positions of the compound. Similarly, when X is nitrogen, the $R_5$ substituent may be located at the 8', 9' or 10' positions of the compound When "c" is 2 and X is carbon, the $R_5$ substituents may be present at any two of the available positions on the ring, i.e., at the 7' and 8', the 9' and 10', the 7' and 9', the 7' and 10', the 8' and 9', or the 8' and 10' positions. When X is nitrogen, the $R_5$ substituents may be present at any two of the available positions on the heterocyclic ring, i.e., at the 8' and 9', the 8' and 10', or 9' and 10' positions. The same reasoning applies when "c" is 3 and X is carbon. When "c" is 3 and X is nitrogen, or when "c" is 4 and X is carbon, all of the available positions on the heterocyclic ring are occupied by substituents.

Similarly, when "e" is 1, the $R_4$ substituents will be located at the 5' or 6' positions of the compound, and when "e" is 2, both of the 5' and 6' positions will be occupied with substituents selected from the aforedescribed group.

While any halogen, i.e., chlorine, bromine, iodine and fluorine, may be used in respect to the aforedescribed halogen or haloalkyl substituents, chlorine and bromine, especially chlorine are preferred for the halogen substituent and fluorine is preferred for the polyhaloalkyl substituent, e.g., trifluoromethyl ($CF_3$). Preferably, $R_4$ is selected from the group consisting of hydrogen, $C_1$-$C_2$ alkyl, e.g., methyl and ethyl, $C_1$-$C_2$ alkoxy, e.g., methoxy and ethoxy, nitro, chloro and bromo; and $R_5$ is selected from the group consisting of hydrogen, $C_1$-$C_2$ alkyl, chloro, fluoro, nitro, $C_1$-$C_2$ trihaloalkyl, e.g., trihalomethyl such as trifluoromethyl, and $C_1$-$C_5$ alkoxy, e.g., methoxy and ethoxy.

$R_6$ of formula I is selected from the group consisting of hydrogen, $C_1$–$C_5$ alkoxy, e.g., $C_1$–$C_3$ alkoxy such as methoxy, $C_1$–$C_5$ alkoxy, e.g., methoxymethoxy, phenoxy, benzyloxy, mono- and di-substituted phenoxy, halogen, e.g., chloro or bromo, $C_1$–$C_5$ thioalkoxy, e.g., thiomethoxy ($CH_3S$—), thiophenoxy, thiobenzyloxy, mono- and di-substituted phenyl and $C_1$–$C_6$ dialkylamino, e.g., dimethylamino. The phenoxy substituents may be the same as those described with respect to $R_4$ and $R_5$ of graphic formula I, particularly $C_1$–$C_3$ alkoxy such as methoxy, and halogen, such as chlorine. The phenyl substituents may be selected from electron donating groups $C_1$–$C_4$ alkyl, $C_1$–$C_2$ alkoxy, and $C_1$–$C_2$ dialkylamino.

Of particular interest, are photochromic materials represented by graphic formula I wherein X is nitrogen, $R_1$ is a $C_1$–$C_4$ alkyl, such as methyl, ethyl, n-propyl, isopropyl, n-butyl, secondary butyl, isobutyl and tertiary butyl; $R_2$, $R_2'$, $R_3$, and $R_3'$ are each hydrogen, methyl, ethyl or phenyl; $R_4$ is hydrogen, methyl, methoxy, nitro, bromo, or chloro; $R_5$ is selected from hydrogen, methoxy, methyl, nitro, bromo or chloro, $R_6$ is hydrogen, methoxy, phenoxy, thiophenoxy, thiomethoxy, chloro or dimethylamino; "c" is 1 or 2, and "e" is 0 or 1. In such compounds, commonly $R_2$ is the same as $R_2'$ and $R_3$ is the same as $R_3'$.

Compounds within the scope of graphic formula I may be named in accordance with International Union of Pure and Applied Chemistry (IUPAC) rules of organic nomenclature. The numbering of the ring system of the spiro (oxazolidine) substituted benzoxazine compounds depicted in formula I is illustrated in the following graphic formula IA.

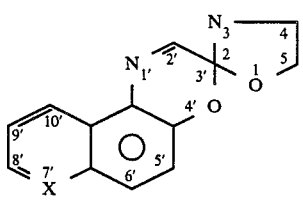

When X is nitrogen, $R_1$, $R_2$, $R_2'$, $R_3$ and $R_3'$ are hydrogen and "c" and "e" are 0, the compound may be named: spiro[oxazolidine-2,3'-[3H] pyrido [3,2-f][1,4]benzoxazine]. When X is carbon in the aforesaid illustration, the compound may be named: spiro[oxazolidine-2,3'-[3H][3,2-f][1,4]naphthoxazine. Examples of compounds within the scope of graphic formula I are tabulated in Table I. These compounds may be named following the aforesaid examples and the numbering system illustrated in graphic formula IA. For example, compound number 1 (X being nitrogen) may be named: 2'-methoxy-3,4,4-trimethylspiro[oxazolidine-2,3'-[3H]pyrido[3,2-f][1,4]benzoxazine]. The remaining compounds of Table I may be similarly named by utilizing the identified substituents and the aforesaid IUPAC rules and numbering system. In compounds 1–24, the $R_4$ and $R_5$ substituent are hydrogen, and X is nitrogen. For compound 25, X is carbon, $R_4$ is hydrogen and $R_5$ is methoxy.

TABLE I

| Compound No. | $R_1$ | $R_2$ | $R_2'$ | $R_3$ | $R_3'$ | $R_6$ |
|---|---|---|---|---|---|---|
| 1 | Me | Me | Me | H | H | MeO |
| 2 | Me | Me | Me | H | H | PhO |
| 3 | Me | Me | Me | H | H | EtO |
| 4 | Me | Me | Me | H | H | iPrO |
| 5 | Me | Me | Me | H | H | H |
| 6 | Me | Me | Me | H | H | p-MeOPhO |
| 7 | Me | Me | Me | H | H | p-ClPhO |
| 8 | Me | Me | Me | H | H | MeS |
| 9 | Me | Me | Me | H | H | t-BuS |
| 10 | Me | Me | Me | H | H | PhS |
| 11 | Me | Me | Me | H | H | Cl |
| 12 | Me | Me | Me | H | H | MeOCH$_2$O |
| 13 | Me | Me | Me | H | H | (Me)$_2$N |
| 14 | Me | Cyclopentyl | | H | H | MeO |
| 15 | Et | Me | Me | H | H | MeO |
| 16 | nPr | Me | Me | H | H | MeO |
| 17 | iPr | Me | Me | H | H | MeO |
| 18 | Me | Ph | Me | H | H | MeO |
| 19 | Me | H | H | Me | Me | MeO |
| 20 | Me | H | H | Ph | Me | MeO |
| 21 | Benzyl | Me | Me | H | H | MeO |
| 22 | Allyl | Me | Me | H | H | MeO |
| 23 | Me | MeOCH$_2$ | MeOCH$_2$ | H | H | MeO |
| 24 | Me | Me | Me | Me | Me | MeO |
| 25 | Me | Me | Me | H | H | MeO; $R_5$ = MeO; X = C |

LEGEND
Et = Ethyl
EtO = Ethoxy
Me = Methyl
MeO = Methoxy
MeS = Thiomethoxy
MeOCH$_2$ = methoxymethyl
MeOCH$_2$O = methoxymethoxy
(Me)$_2$N = dimethylamino
p-MeOPhO = para-methoxyphenoxy
Cl = chloro
iPr = Isopropyl
iPrO = isopropoxy
nPr = n-propyl
Ph = phenyl
PhO = phenoxy
p-ClPhO = para-chlorophenoxy
PhS = thiophenoxy
t-BuS = thio-t-butyloxy The photochromic materials of the present invention can be dissolved in common organic solvents such as benzene, toluene, chloroform, ethylacetate, methylethylketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine, and ethylene glycol.

The photochromic materials of the present invention can also be dissolved in colorless or transparent solutions prepared from transparent polymers, copolymers or blends of such transparent polymers or copolymers and a suitable organic solvent, e.g., polymers of trasparent host materials described hereinafter dissolved in one or more of the aforesaid described organic solvents. Examples of such solutions include a polyvinylacetate-acetone solution, a nitrocellulose-acetonitrile solution, a polyvinylchloride-methylethylketone solution, a polymethylmethacrylate-acetone solution, a cellulose acetate-dimethylformamide solution, a polyvinylpyrrolidone-acetonitrile solution, a polystyrene-benzene solution, and an ethyl cellulose-methylene chloride solution.

The aforesaid photochromic solutions or compositions can be applied to a transparent support, such as cellulose triacetate, polyethylene terephthalate or baryta paper and dried to obtain a photochromic material, which may be color formed by ultraviolet radiation and returned to colorless by removing the source of ultraviolet radiation.

The photochromic materials of the present invention or compositions containing same can be applied to or incorporated within a solid polymerized organic material, i.e., a synthetic plastic host material. Preferably, the host material is a transparent or optically clear material, e.g., materials suitable for ophthalmic elements, such as ophthalmic lenses, or materials useful for applications such as windows, windshields, etc. A host material containing the photochromic compounds of the present invention can be used in the preparation of photochromic plastic films, sheets and lenses, such as lenses for sunglasses, ski goggles, visors, camera lenses and filters. As used herein, the term "optical element" is meant to include lenses and transparencies.

In general, photochromic materials of the present invention can be incorporated into organic coatings, e.g., coatings containing the aforedescribed polymers or copolymers, or other polymeric materials. More particularly, the photochromic materials may be used in printing inks and other coatings, including pigmented coatings, such as paints.

Examples of host materials that may be used with the photochromic compounds of the present invention include: polymers of polyol(allyl carbonate) monomers and copolymers thereof, polyacrylates, (alkylacrylates) poly(alkylacrylates) such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethyleneterephthalate, polystyrene, poly(styrene-methylmethacrylate) copolymers, poly(styrene-acrylonitrile) copolymer, and polyvinylbutyral. Transparent copolymers of the above-described monomers and blends of the transparent polymers are also suitable as host materials.

Preferably, the host material is an optically clear polymerized organic material prepared from a polycarbonate, such as poly(4,4'-dioxydiphenol-2,2-propane), which is sold under the trademark, LEXAN; a polymethylmethacrylate, such as material sold under the trademark, PLEXIGLAS; polymerizates of a polyol(allyl carbonate), especially diethylene glycol bis(allyl carbonate) which is sold under the trademark, CR-39, and its copolymers with for example vinyl acetate, e.g., copolymers of from 80-90 percent diethylene glycol bis(allyl carbonate) and 10-20 percent vinyl acetate, particularly 80-85 percent of the bis(allyl carbonate) and 15-20 percent vinyl acetate; cellulose acetate, cellulose propionate, cellulose butyrate; polystyrene and its copolymers with methyl methacrylate, vinyl acetate and acrylonitrile; and cellulose acetate butyrate.

Polyol (allyl carbonate) monomers which can be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., U.S. Pat. Nos. 2,370,567 and 2,403,113.

The polyol (allyl carbonate) monomers can be represented by the graphic formula:

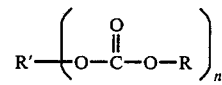

wherein R is the radical derived from an unsaturated alcohol and is commonly an allyl or substituted allyl group, R' is the radical derived from the polyol, and n is a whole number from 2–5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

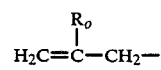

wherein $R_o$ is hydrogen, halogen, or a $C_1$–$C_4$ alkyl group. Specific examples of R include the groups: allyl, 2-chloroallyl, 2-bromoallyl, 2-fluoroallyl, 2-methallyl, 2-ethylallyl, 2-isopropylallyl, 2-n-propylallyl, and 2-n-butylallyl. Most commonly, R is allyl, i.e., $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, diethylene glycol, triethylene glycol, etc.

The aromatic polyol can be represented by the graphic formula:

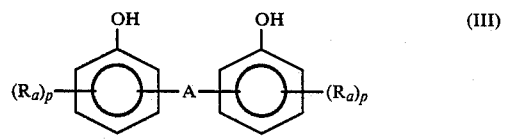

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene(isopropylidene), $R_a$ represents lower alkyl substituents of from 1 to 3 carbon atoms, and p is 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as $-CH_2O-CH_2-$, $-CH_2CH_2-O-CH_2CH_2-$, $-CH_2-O-CH_2-CH_2-$, and $-CH_2CH_2CH_2-O-CH_2CH_2CH_2-$; alkylene polyether groups such as $-CH_2CH_2-O-CH_2CH_2-O-CH_2CH_2-$ and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2C-$ H₂—O—CH₂CH₂—O—CO—O—CH₂CH₂—O—CH₂CH₂—; and isopropylidene bis(para-phenyl), i.e.,

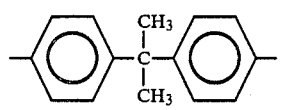 (IV)

Most commonly, R' is —CH₂CH₂—, —CH₂CH₂—O—CH₂CH₂—, or —CH₂CH₂—O—CH₂CH₂—O—CH₂CH₂—.

Specific examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which can be utilized in the invention herein contemplated are:

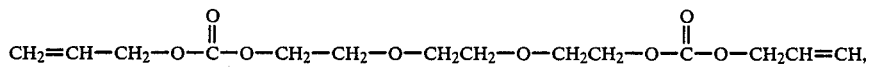 (V)

Triethylene Glycol bis(Allyl Carbonate)

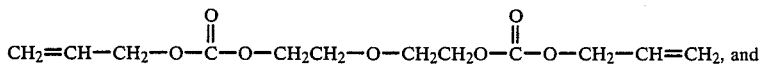 (VI)

Diethylene Glycol bis(Allyl Carbonate)

 (VII)

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

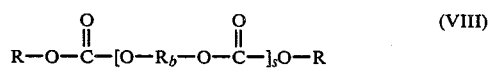 (VIII)

wherein R is as defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula, wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer can be used. In that embodiment, the monomer is thickened by heating or partially polymerized by using small amounts of initiator, e.g., 0.5–1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

The amount of the photochromic compound or composition-containing same applied to or incorporated into a host material is not critical and depends generally upon the intensity of the color of the composition desired upon irradiation thereof and upon the method used to incorporate or apply the photochromic compound. Typically, the more compound added, the greater the color intensity. Generally such amount can be described as a photochromic amount. Usually, the amount of photochromic compound incorporated into the host material ranges from about 0.01 to about 20 percent by weight, more usually from about 0.05 to about 10 percent by weight, based on the weight of the host material. Stated another way, the amount of photochromic compound used to impart a photochromic effect will typically vary from about 1 to about 50, e.g., 1 to 10, milligrams of the photochromic compound per square inch of the surface of the host material independent of the thickness of the host material article. Hence, the photochromic compound is present in a higher concentration in thin samples, films, or coatings, and in a lower concentration in thick samples.

Solutions of the photochromic compounds of the present invention undergo a change in color upon exposure to ultraviolet radiation and return to their original color or colorless state upon removal of the source of ultraviolet radiation. Such color change may be repeated numerous times.

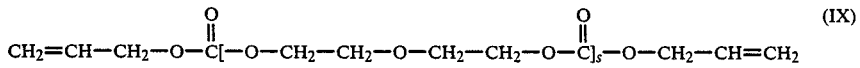 (IX)

The photochromic compounds or compositions of the present invention can be applied to or incorporated into a host material by methods known in the art. Such methods include dissolving or dispersing the compound in the host material, i.e., imbibation of the photochromic compound in the host material, by immersion, thermal transfer, or coating, and incorporation of the photochromic compound as a separate layer between adjacent layers of the host material. The term "imbibation" or "imbibe" is intended to mean and include diffusion of the photochromic compound alone into the host material, solvent assisted diffusion, absorption of the photochromic compound into a porous polymer, vapor phase transfer, and other such transfer mechanisms. For example:

(a) The photochromic compounds or compositions of the present invention can be mixed with a polymerizable composition that, upon curing, produces an optically clear polymeric host material and the polymerizable composition cast as a film, sheet or lens, or injection molded or otherwise formed into a sheet or lens;

(b) The photochromic compounds of the present invention can be dissolved or dispersed in polar or nonpolar aprotic organic solvents or solvent mixtures and then imbibed into the solid host material by immersion for from several minutes to several hours, e.g., 2–3 minutes to 2–3 hours of the host material in a bath of such solution or dispersion. The bath is conventionally at an elevated temperature, usually in the range of 50°–120° C. Thereafter, the host material is removed from the bath and dried;

(c) The photochromic compounds and compositions may also be applied to the surface of the host material by any convenient manner, such as spraying, brushing, spin-coating or dip-coating from a solution or dispersion of the photochromic material in the presence of a polymeric binder. Thereafter, the photochromic compound is imbibed by the host material by heating it, e.g., in an oven, for from a minute to several hours at temperatures in the range of from 80°–180° C.;

(d) In a variation of the above imbibition procedure, the photochromic compound or composition can be deposited onto a temporary support, e.g., a sheet of kraft paper, aluminum foil, polymer film or fabric, which is then placed in contact with the host material and heated, e.g., in an oven;

(e) The photochromic compounds can be dissolved or dispersed in a transparent polymeric material which can be applied to the surface of the host in the form of an adherent film by any suitable technique such as spraying, brushing, spin-coating or dip-coating; and (f) Finally, the photochromic compounds can be incorporated or applied to a transparent polymeric material by any of the above-mentioned methods, which can then be placed within the host material as a discrete layer intermediate to adjacent layers of the host material.

The photochromic materials of the present invention may be synthesized by condensing an appropriately substituted 2-alkylideneoxazoline with an ortho-nitrosohydroxy aromatic in a hydrocarbon solvent at reflux conditions followed by isolation and purification by chromatography, crystallization, distillation or trituration. The required precursor materials, i.e., oxazolidinium salts and nitrosohydroxy aromatic compounds, may be synthesized using procedures available in the literature. Briefly, the oxazolidinium salts are prepared by condensation of alpha-substituted acetic acids with various beta-hydroxyamines followed by reaction of the oxazoline with an alkyl halide. See, for example, "Hydrolysis of N-Methyl-2,4,4-substituted$\Delta^2$-Oxazolinium Iodides" by Paul Allen, Jr. et al, Journal of Organic Chemistry, Vol. 28, pp. 2759–2762 (October, 1963). The nitrosohydroxy aromatic compounds are made by reaction of aromatic hydroxy compounds with sodium nitrite in an acidic medium. See, for example, Organic Synthesis, Volume I, 2nd Edition, H. Gilman et al, Ed., John Wiley and Sons, pp. 411–413 (1941).

The present invention is more particularly described in the following examples which are intended as illustrative only since numerous modifications and variations therein will be apparent to those skilled in the art.

EXAMPLE 1

(Method A)

Into a dry 100 milliliter (ml) three-necked flask kept under dry nitrogen and fitted with a reflux condenser and internal thermometer was added 2-methoxymethyl-3,4,4-trimethyl-1,3-oxazolidinium iodide (2.85 grams, 10 mmole) and 30 ml dry benzene. To the heterogeneous stirred solution was added in one portion triethylamine (1.52 grams, 15 mmole) and the solution heated to reflux before adding solid 5-nitroso-6-quinolinol (1.74 grams, 10 mmole) in small portions over 30 minutes. The resultant grown solution was heated at reflux for about 4 hours and then cooled with stirring overnight. The solution was then decanted away from the tarry residue, concentrated in vacuo, and the product isolated by flash chromatography to yield 0.29 grams of 2'-methoxy-3,4,4-trimethylspiro[oxazolidine-2,3'-[3H]pyrido[2,2-f][1,4]benzoxazine], which was characterized by appropriate spectral techniques. A toluene solution of the product changed to red when irradiated with ultraviolet light. The solution returned to its original hue after the UV light was removed.

(Method B)

Into a dry 250 ml three-necked flask kept under dry nitrogen and fitted with a reflux condenser and internal thermometer was added 2-methoxymethyl-3,4,4-trimethyl-1,3-oxazolidinium iodide (7.13 grams, 25 mmole), powdered potassium carbonate (8.97 grams, 65 mmole) and 125 ml dry benzene. The heterogeneous mixture was heated at 70° C. for 90 minutes before addition of 5-nitroso-6-quinolinol (5.44 grams, 25 mmole). The resulting reaction mixture was heated at 70° C. for 17 hours, cooled and filtered through Celite ® diatomaceous earth powder. The solvent was removed in vacuo from the filtrate, and the resulting residue purified by flash chromatography to yield 0.33 grams of 2'-methoxy-3,4,4-trimethylspiro [oxazolidine-2,3'-[3H] pyrido [3,2-f] [1,4] benzoxazine].

EXAMPLE 2

Into a dry 250 ml three-necked flask kept under dry nitrogen and fitted with a distillation column and internal thermometer was added 2-phenoxymethyl-3,4,4-trimethyl-1,3-oxazolidinium iodide (6.00 grams, 18.1 mmole) and 80 ml dry benzene. To the heterogeneous stirred solution was added in one portion triethylamine (3.64 grams, 36 mmole) followed by 5-nitroso-6-quinolinol (2.61 grams, 15 mmole). The solution was heated to reflux and maintained at reflux for 3 hours during which time water that formed during the course of the reaction was azeotropically removed. The solution was cooled with stirring overnight, decanted away from the tarry residue, and concentrated in vacuo. The product was isolated by flash chromatography to yield 0.16 grams of 2'-phenoxy-3,4,4-trimethylspiro[oxazolidine-2,3'-[3H]pyrido[3,2-f] [1,4]benzoxazine], which was characterized by appropriate spectral techniques. A toluene solution of the product changed to red when irradiated with ultraviolet light. The solution returned to its original hue after the UV light was removed.

EXAMPLE 3

Into a dry 250 ml three-necked flask kept under dry nitrogen and fitted with a reflux condenser and internal thermometer was added 2-ethoxymethyl-3,4,4-trimethyl-1,3-oxazolidinium iodide (5.94 grams, 20 mmole), powdered potassium carbonate (6.21 grams, 45 mmole), and 100 ml dry benzene. The heterogeneous mixture was heated at 65° C. for 90 minutes before addition of 5-nitroso-6-quinolinol (3.48 grams, 20 mmole). The resulting reaction mixture was heated at 65° C. for 6 hours and the reaction cooled with stirring. The reaction mixture was filtered through Celite ® diatomaceous earth, the solvent removed in vacuo from the filtrate and the resulting residue purified by flash chromatography. The presence of the compound 2'-ethoxy-3,4,4-trimethylspiro [oxazolidine-2,3'-[3H] pyrido [3,2-f] [1,4] benzoxazine] in the isolated product was verified spectroscopically. A solution of the isolated product in a 30% ethyl acetate/70% hexane mixture changed to red when irradiated with ultraviolet light. The solution returned to its original hue after the UV light was removed.

EXAMPLE 4

The procedure of Example 1, method A, was followed using 6.38 grams (25 mmole) of 2,3,4,4-tetramethyl-1,3-oxazolidinium iodide, 50 mmole triethylamine and 5.44 grams (25 mmole) of 5-nitroso-6-quinolinol as the starting materials. A solution of the product, i.e., 3,4,4-trimethylspiro [oxazolidine-2,3'-[3H] pyrido [3,2-f] [1,4] benzoxazine], in a 2:1 heaxane:ethyl acetate mixture changed to red when irradiated with ultraviolet light. The solution returned to its original hue after the UV light was removed.

EXAMPLE 5

The procedure of Example 1, Method A, was followed using 3.51 grams (15 mmole) of 3-allyl-2,4,4-trimethyl-1,3-oxazolidinium bromide, 30 mmole of triethylamine and 3.26 grams (15 mmole) of 5-nitroso-6-quinolinol as the starting materials. Solid potassium carbonate was also added to the reaction mixture as a water scavenger. The presence of the compound 3-allyl-4,4-dimethylspiro [oxazlidine-2,3'-[3H] pyrido [3,2-f] [1,4] benzoxazine] in the isolated product was verified spectroscopically. A solution of the isolated product in a 40% ethyl acetate/60% hexane mixture changed to red when irradiated with ultraviolet light. The solution returned to its original hue after the UV light was removed.

EXAMPLE 6

The procedure of Example 1, Method A, was followed using 5.28 grams (20 mmole) of 3-allyl-4,4-dimethyl-2-methoxymethyl-1,3-oxazolidinium bromide, 30 mmole of triethylamine and 3.48 grams (20 mmole) of 5-nitroso-6-quinolinol as the starting reactants. Solid potassium carbonate was also added to the reaction mixture as a water scavenger. The presence of the compound 3-allyl-4,4-dimethyl-2'-methoxyspiro [oxazolidine-2,3'-[3H] pyrido [3,2-f] [1,4] benzoxazine] in the isolated product was verified spectroscopically. A solution of the isolated product in a 50/50 ethyl acetate/hexane mixture changed to red when irradiated with ultraviolet light. The solution returned to its original hue after the UV light was removed.

Although the present invention has been described with reference to specific details of certain embodiments thereof, it is not intended that such details should be regarded as limitations upon the scope of the invention except as and to the extent that they are included in the accompanying claims.

We claim:

1. A compound represented by the following graphic formula:

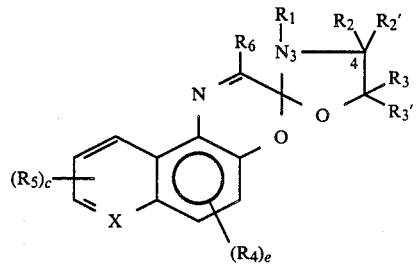

wherein:
(a) $R_1$ is selected from the group consisting of $C_1$–$C_8$ alkyl, $C_2$–$C_5$ alkenyl, phenyl, benzyl, and mono- and di-substituted phenyl, said phenyl substituents being selected from $C_1$–$C_4$ alkyl and $C_1$–$C_5$ alkoxy;
(b) $R_2$, $R_2'$, $R_3$ and $R_3'$ are each selected from the group consisting of hydrogen, $C_1$–$C_5$ alkyl, $C_1$–$C_4$ alkoxyalkyl, phenyl, and mono- and di-substituted phenyl, said phenyl substituents being selected from $C_1$–$C_4$ alkyl and $C_1$–$C_5$ alkoxy; or $R_2$ and $R_2'$ or $R_3$ and $R_3'$ combine to form a $C_3$–$C_6$ cycloalkyl;
(c) $R_4$ and $R_5$ are each selected from the group consisting of hydrogen, $C_1$–$C_5$ alkyl, $C_1$–$C_5$ alkoxy, phenyl, phenoxy, mono- and di-substituted phenoxy, nitro, cyano, $C_1$–$C_4$ monohaloalkyl, $C_1$–$C_4$ polyhaloalkyl, $C_1$–$C_4$ alkylsulfonyl, trihaloacetyl, benzoyl, benzoyloxy, and $C_1$–$C_4$ acyloxy, said phenoxy substituents being selected from electron donating and electron withdrawing groups;
(d) $R_6$ is selected from the group consisting of hydrogen $C_1$–$C_5$ alkoxy, $C_1$–$C_5$ alkoxy-$C_1$–$C_5$ alkoxy, phenoxy, benzyloxy, mono- and di-substituted phenoxy, halogen, $C_1$–$C_5$ thioalkoxy, thiophenoxy, thiobenzyloxy, mono- and di-substituted phenyl and $C_1$–$C_6$ dialkylamino, said phenoxy substituents being selected from electron donating and electron withdrawing groups, and said phenyl substituents being selected from $C_1$–$C_4$ alkyl, $C_1$–$C_2$ alkoxy and $C_1$–$C_2$ dialkylamino groups;
(e) X is nitrogen or carbon; and
(f) the letters "c" and "e" are numbers from 0 to 4 and 0 to 2 respectively.

2. A compound of claim 1 wherein:
(a) $R_1$ is a $C_1$–$C_4$ alkyl, $C_2$–$C_3$ alkenyl, benzyl or phenyl;
(b) $R_2$, $R_2'$, $R_3$ and $R_3'$ are each selected from hydrogen, $C_1$–$C_5$ alkyl, phenyl, or methoxymethyl;

(c) R$_4$ is selected from hydrogen, C$_1$-C$_2$ alkyl, C$_1$-C$_2$ alkoxy, nitro, chloro or bromo; R$_5$ is selected from hydrogen, C$_1$-C$_2$ alkyl, chloro, fluoro, nitro, C$_1$-C$_2$ trihaloalkyl, or C$_1$-C$_5$ alkoxy;

(d) R$_6$ is hydrogen C$_1$-C$_5$ alkoxy, phenoxy, thiophenoxy, thiomethoxy, chloro, or C$_1$-C$_6$ dialkylamino; and (e) the letters "c" and "e" are numbers from 0 to 2 and 0 to 1 respectively.

3. A compound of claim 1 wherein the electron donating group is selected from the group consisting of C$_1$-C$_4$ alkyl, C$_1$-C$_4$ alkoxy, amino, monoalkylamino and dialkylamino in which the alkyl groups contain from 1 to 6 carbon atoms, and the electron withdrawing group is selected from the group consisting of cyano, nitro, chloro, fluoro and C$_1$-C$_4$ trihaloalkyl.

4. A compound of claim 2 wherein:
(a) R$_1$ is a C$_1$-C$_4$ alkyl,
(b) R$_2$, R$_2'$, R$_3$ and R$_3'$ are each hydrogen, methyl, ethyl or phenyl,
(c) R$_4$ and R$_5$ are each hydrogen, methyl, methoxy, nitro, bromo, or chloro,
(d) R$_6$ is hydrogen, methoxy, phenoxy, thiophenoxy, thiomethoxy, chloro, or dimethylamino,
(e) X is nitrogen, and
(f) the letter "c" is 1 or 2, and the letter "e" is 0 or 1.

5. A compound of claim 4 wherein R$_2$ and R$_2'$ are the same, and R$_3$ and R$_3'$ are the same.

6. A compound of claim 5 wherein R$_2$, R$_2'$, R$_3$ and R$_3'$ are hydrogen.

7. A compound of claim 2 wherein:
(a) R$_1$ is a C$_1$-C$_4$ alkyl,
(b) R$_2$, R$_2'$, R$_3$ and R$_3'$ are each hydrogen, methyl, ethyl or phenyl,
(c) R$_4$ and R$_5$ are each hydrogen, methyl, methoxy, nitro, bromo, or chloro,
(d) R$_6$ is hydrogen, methoxy, phenoxy, thiophenoxy, thiomethoxy, chloro, or dimethylamino,
(e) X is carbon, and
(f) the letter "c" is 1 or 2, and the letter "e" is 0 or 1.

8. An article comprising an organic host material containing a photochromic amount of a photochromic compound represented by the following graphic formula:

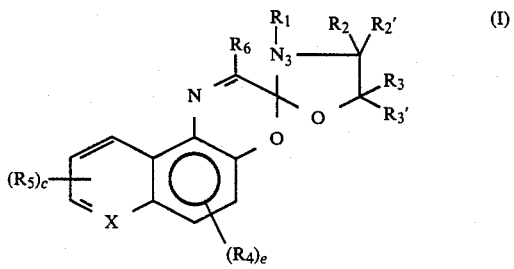

(I)

wherein:
(a) R$_1$ is selected from the group consisting of C$_1$-C$_8$ alkyl, C$_2$-C$_5$ alkenyl, phenyl, benzyl, and mono- and di-substituted phenyl, said phenyl substituents being selected from C$_1$-C$_4$ alkyl and C$_1$-C$_5$ alkoxy;

(b) R$_2$, R$_2'$, R$_3$ and R$_3'$ are each selected from the group consisting of hydrogen, C$_1$-C$_5$ alkyl, C$_1$-C$_4$ alkoxyalkyl, phenyl, and mono- and di-substituted phenyl, said phenyl substituents being selected from C$_1$-C$_4$ alkyl and C$_1$-C$_5$ alkoxy; or R$_2$ and R$_2'$ or R$_3$ and R$_3'$ combine to form a C$_3$-C$_6$ cycloalkyl;

(c) R$_4$ and R$_5$ are each selected from the group consisting of hydrogen, C$_1$-C$_5$ alkyl, C$_1$-C$_5$ alkoxy, phenyl, phenoxy, mono- and di-substituted phenoxy, nitro, cyano, C$_1$-C$_4$ monohaloalkyl, C$_1$-C$_4$ polyhaloalkyl, C$_1$-C$_4$ alkylsulfonyl, trihaloacetyl, benzoyl, benzoyloxy, and C$_1$-C$_4$ acyloxy, said phenoxy substituents being selected from electron donating and electron withdrawing groups;

(d) R$_6$ is selected from the group consisting of hydrogen C$_1$-C$_5$ alkoxy, C$_1$-C$_5$ alkoxy-C$_1$-C$_5$ alkoxy, phenoxy, benzyloxy, mono- and di-substituted phenoxy, halogen, C$_1$-C$_5$ thioalkoxy, thiophenoxy, thiobenzyloxy, mono- and di-substituted phenyl and C$_1$-C$_6$ dialkylamino, said phenoxy substituents being selected from electron donating and electron withdrawing groups, and said phenyl substituents being selected from C$_1$-C$_4$ alkyl, C$_1$-C$_2$ alkoxy and C$_1$-C$_2$ dialkylamino groups;

(e) X is nitrogen or carbon; and (f) the letters "c" and "e" are numbers from 0 to 4 and 0 to 2 respectively.

9. The article of claim 8 wherein the organic host material is selected from the group consisting essentially of polymers of polyol(allyl carbonate), copolymers of polyol(allyl carbonate) and vinyl acetate, polyacrylates, poly(alkylacrylates), cellulose acetate, cellulose triacetate, cellulose acetate propionate, cellulose acetate butyrate, poly(vinyl acetate), poly(vinyl alcohol), polycarbonate, polystyrene, poly(styrene-methylmethacrylate)copolymers, poly(styrene-acrylonitrile)copolymers, and polyvinyl butyral.

10. The article of claim 8 wherein the organic host material includes a polyol(allyl carbonate).

11. The article of claim 10 wherein the polyol(allyl carbonate) is diethylene glycol bis(allyl carbonate).

12. The article of claim 8 wherein the article is an ophthalmic article.

13. The article of claim 12 wherein the ophthalmic article is a lens.

14. The article of claim 12 wherein the organic host material includes a polyol(allyl carbonate).

15. 2'-methoxy-3,4,4-trimethylspiro [oxazolidine-2,3'-[3H] pyrido [3,2-f] [1,4] benzoxazine].

16. 2'ethoxy-3,4,4-trimethylspiro [oxazolidine-2,3'-[3H] pyrido[3,2-f] [1,4] benzoxazine].

17. 3,4,4-trimethylspiro [oxazolidine-2,3'-[3H] pyrido [3,2-f] [1,4] benzoxazine].

18. 3-allyl-4,4-dimethylspiro [oxazolidine-2,3'-[3H] pyrido [3,2-f] [1,4] benzoxazine].

19. 3-allyl-4,4-dimethyl-2'-methoxyspiro [oxazolidine-2,3'-[3H] pyrido [3,2-f] [1,4] benzoxazine].

* * * * *